United States Patent [19]
Haber et al.

[11] Patent Number: 5,122,117
[45] Date of Patent: Jun. 16, 1992

[54] COMPONENT MIXING SYRINGE

[75] Inventors: Terry M. Haber, Lake Forest; Clark B. Foster, Laguna Niguel; William H. Smedley, Lake Elsinore, all of Calif.

[73] Assignee: Habley Medical Technology Corp., Laguna Hills, Calif.

[21] Appl. No.: 533,734

[22] Filed: Jun. 5, 1990

[51] Int. Cl.⁵ .............................................. A61M 37/00
[52] U.S. Cl. ...................................... 604/90; 604/201
[58] Field of Search ................ 604/82, 86, 89–91, 604/110, 188, 191, 201, 202, 203, 206, 213, 240, 256

[56] References Cited

U.S. PATENT DOCUMENTS

| | | | |
|---|---|---|---|
| 2,675,804 | 4/1954 | Krug | 604/89 |
| 3,477,431 | 11/1969 | Walecka | 604/89 |
| 3,747,812 | 7/1973 | Karman et al. | 604/110 |
| 4,059,109 | 11/1977 | Tischlinger | 604/90 |
| 4,668,223 | 5/1987 | Grotenhuis | 604/191 |
| 4,755,169 | 7/1988 | Sarnoff et al. | 604/89 |
| 4,758,230 | 7/1988 | Rycroft | 604/206 |
| 4,841,985 | 6/1989 | Wanamaker | 604/240 |
| 4,874,377 | 10/1989 | Newgard et al. | 604/256 |
| 4,886,495 | 12/1989 | Reynolds | 604/191 |
| 4,931,040 | 6/1990 | Haber et al. | 604/110 |

Primary Examiner—C. Fred Rosenbaum
Assistant Examiner—Sharon Finkel
Attorney, Agent, or Firm—Townsend and Townsend

[57] ABSTRACT

A component mixing syringe (2) is used to mix a liquid component (94) with a solid component (96) prior to use. The syringe includes a barrel (4) having a bore (10) with a plunger (20) at one end and a needle (54) at the other. A barrier (14) divides the bore into a far region (16) and a near region (18). The far region is divided into variable volume liquid and air compensating regions (88, 90) which contain the liquid and dry components. The plunger is partially withdrawn from the near region to create a partial vacuum. A pathway formed through the barrier is opened to permit the liquid to rush into the near region to create a relatively violent, turbulent mixing action to effectively mix the two components. The mixing can be further enhanced by moving the plunger along the bore forcing the mixture back and forth between the near and far regions. Once mixed, the pathway between the near and far regions is sealed and a pathway between the needle and the mixture in the near region is opened so that depressing the plunger forces the mixture through the needle.

23 Claims, 4 Drawing Sheets

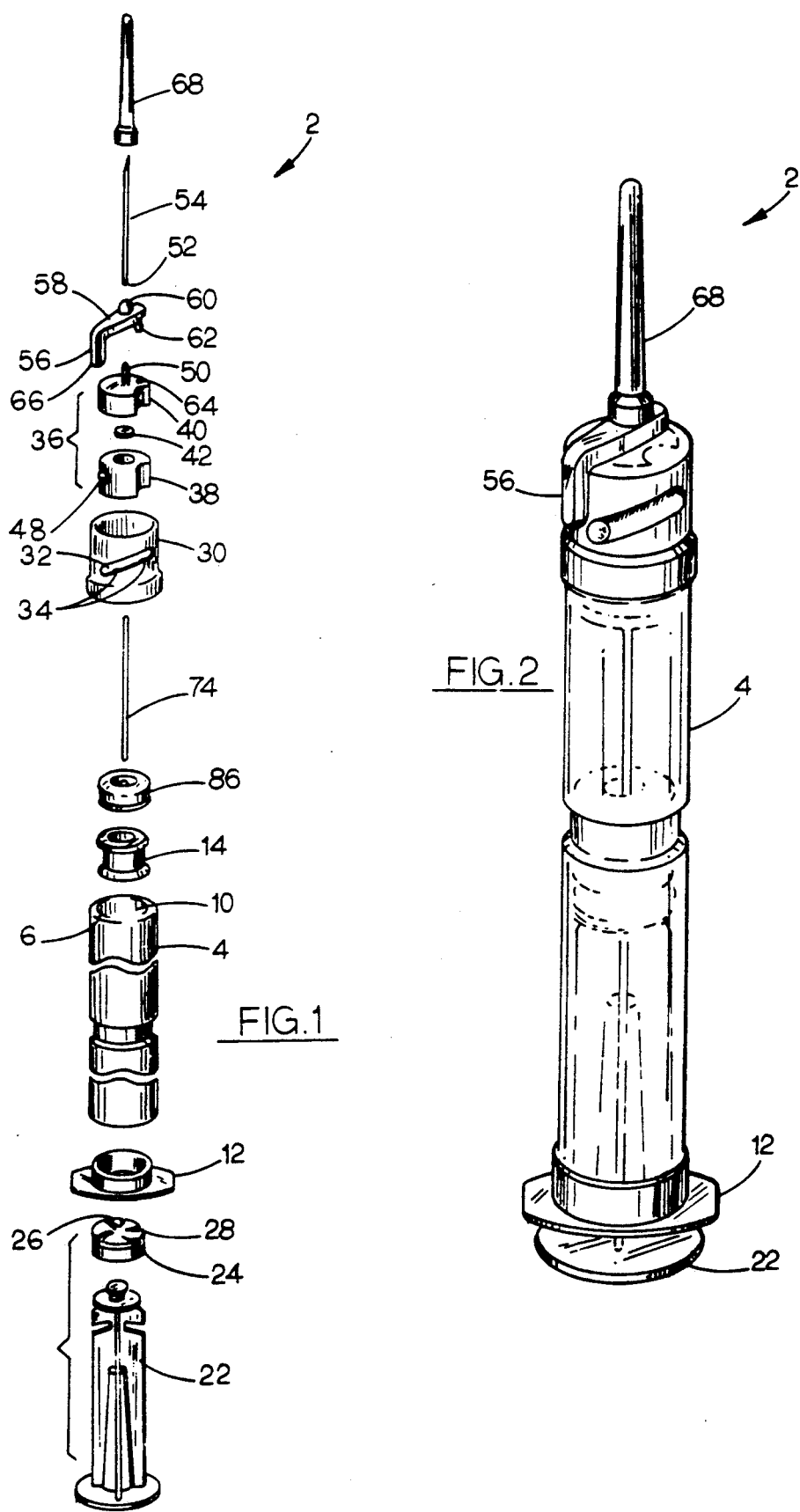

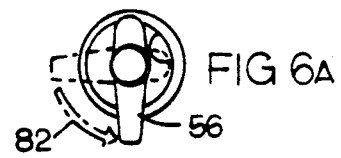
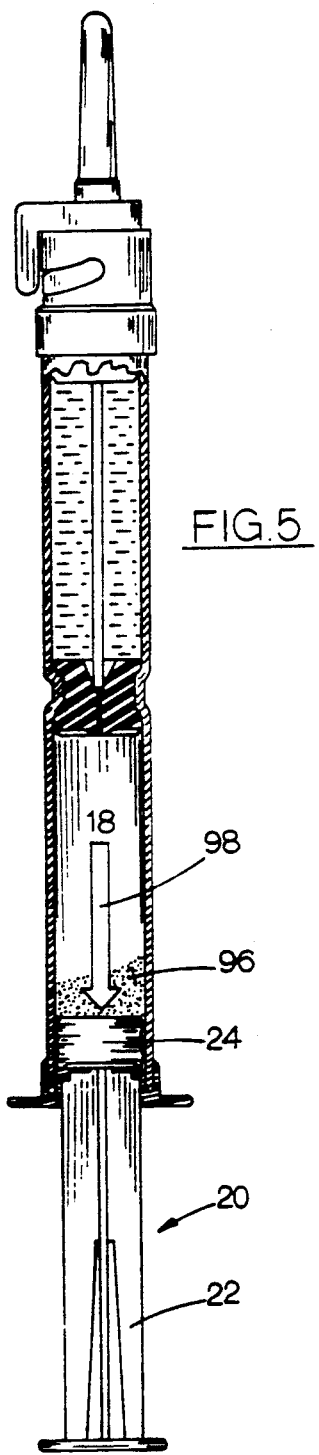
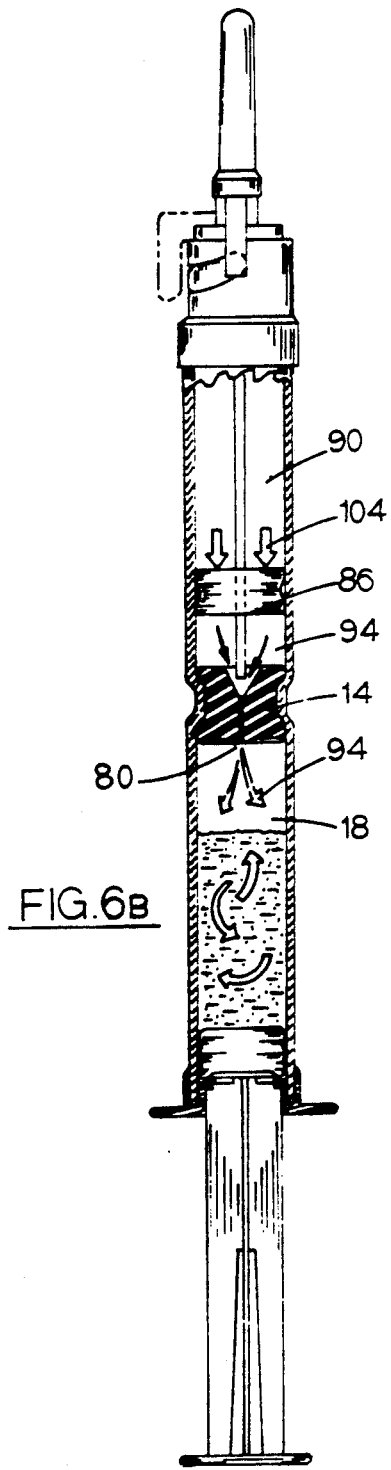

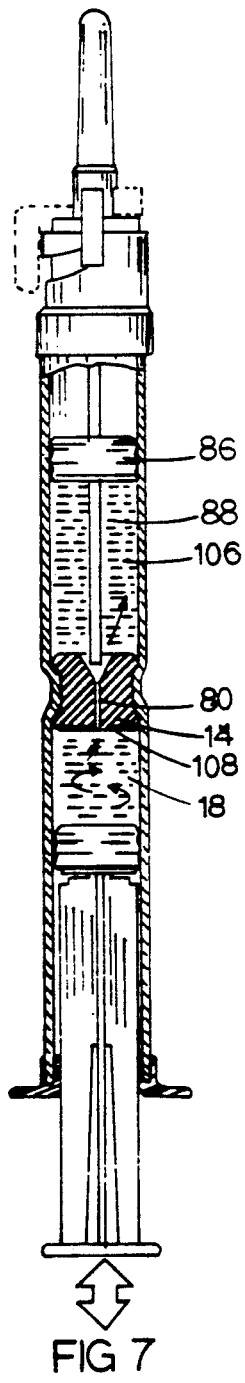
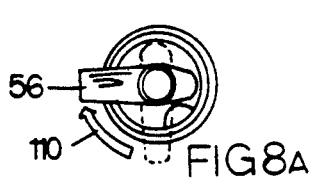
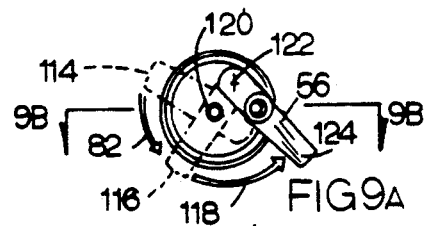
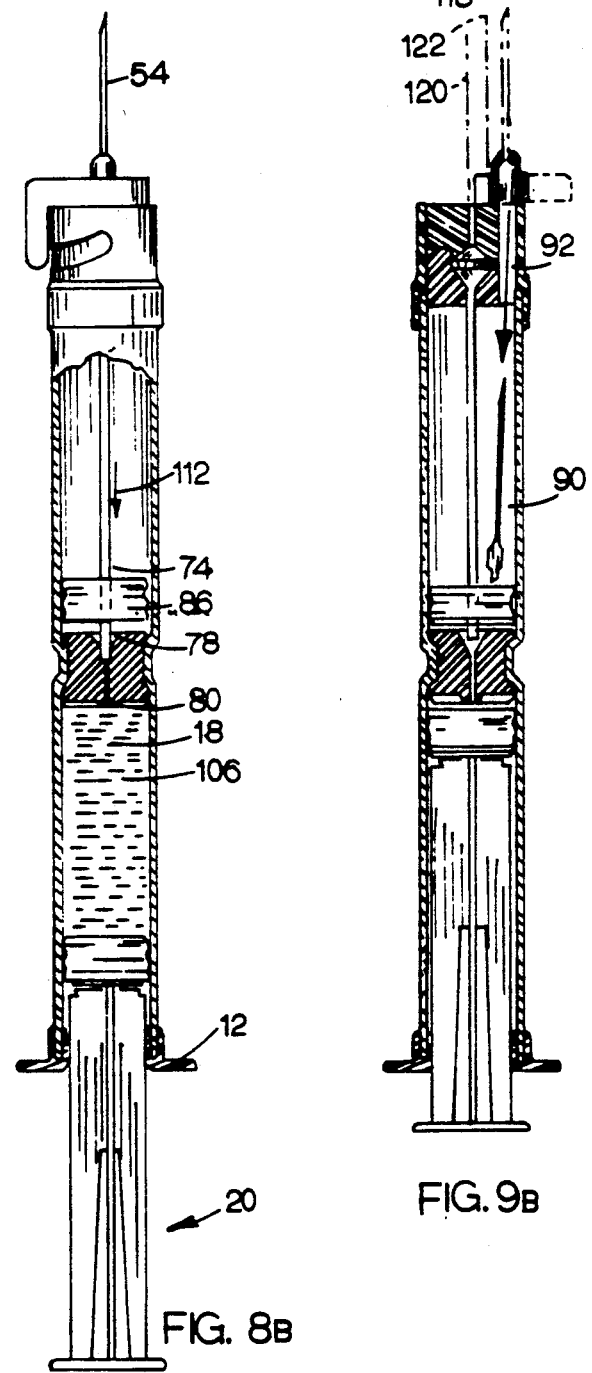
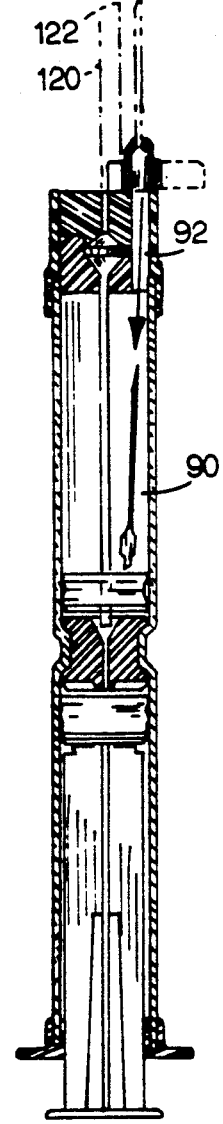
FIG 7
FIG. 8A
FIG. 8B
FIG. 9A
FIG. 9B

COMPONENT MIXING SYRINGE

BACKGROUND OF THE INVENTION

Some medicines have a very short shelf-life unless kept refrigerated. For example, TPA, used in treating heart attacks, must be kept under refrigeration when in its liquid form.

One way to extend the room temperature shelf-life of some medicines is by removing the liquid from the medicine and storing the medicine in a dry form. When the medicine is to be used, liquid, typically sterile water, is added to the dry medicine to reconstitute the medicine to its liquid form. If the medicine is to be taken orally, the thoroughness of mixing is generally not a great problem. However, many medicines are injected into the user. In these cases, the mixing must be especially thorough and complete.

Hydrating syringes have been developed to store the dry and liquid components of the medicine in separate compartments. The compartments are fluidly connected, the contents are mixed together and then the mixture is injected into the patient. One of the problems with these prior art hydrating syringes is that incomplete mixing often occurs leaving a residue of the dry component in the syringe. Incomplete mixing of the dry and liquid components of the medicine may be caused at least in part when mixing is restricted to one pass of the liquid component into the region of the syringe containing the solid component. Thus, existing hydrating syringes are not as efficient or effective as may be desired.

SUMMARY OF THE INVENTION

The present invention is directed to a component mixing syringe, preferably a hydrating syringe by which a liquid component is mixed with a dry component. The components are under the influence of a differential pressure between the regions within which the components are contained to provide superior turbulent mixing action of the components.

The syringe includes a barrel having a bore along its length. A plunger is mounted to one end of the barrel and a needle is mounted to the other end. The bore is divided into two regions by a barrier. A distal or far region is created between the barrier and the needle end of the barrel. A proximal or near region is defined between the barrier and the plunger. A first, liquid component is housed within the far region while a second, typically dry component is housed within the near region.

A differential pressure between the near and far regions is created, typically by drawing the plunger partially out of the near region of the bore to create a partial vacuum within the near region. While subjected to this partial vacuum, a pathway, typically formed through the barrier, is opened to permit the liquid within the far region to rush into the near region. This rush of liquid creates a relatively violent, turbulent mixing action to effectively mix the two components. The mixing can be further enhanced by moving the plunger along the bore forcing the mixture back and forth between the near and far regions.

Once mixed, and with the mixture in the near region, the pathway between the near and far regions is sealed and a path from the near region through the needle is opened so that depressing the plunger forces the mixture through the needle.

Preferably a hollow tube fluidly connects the needle with the pathway formed through the barrier connecting the near and far regions. The hollow tube is mounted to a hub assembly at the needle end of the barrel. The hub assembly, and the hollow tube therewith, are movable axially so that the hollow tube can be moved to seal the pathway formed in the barrier thus separating the near and far regions. With the path from the hollow tube through the needle sealed, typically by the use of a sheath covering the needle, a partial vacuum can be drawn within the near region by partially withdrawing the plunger. Moving the hollow tube axially opens the pathway and permits the liquid in the far region to rush into the near region. With the mixture in the near region, sealing the pathway in the barrier with the hollow tube permits the dispensing of the mixture through the pathway, the hollow tube and finally out the needle, from which the sheath has been removed. Thus, the hollow tube serves the dual functions of sealing the pathway in the barrier and fluidly coupling the near region to the bore in the hub assembly.

Another feature of the preferred embodiment the invention relates to the use of a selector arm which not only causes the hollow tube to move axially by rotating the hub assembly, which is mounted within a cam sleeve secured to the barrel, but can also be used to disable the syringe after use. The cam sleeve includes a generally spiral cam slot; the cam assembly includes a cam pin which rides within the cam slot. Therefore, rotation of the hub assembly within the cam sleeve causes the hub assembly to move axially within the cam sleeve. The hub assembly includes an axially positioned frangible connecting tip to which the base of the needle is secured. The selector arm is pivotally mounted over the frangible connecting tip. The selector arm has an eccentric drive pin which engages an eccentric hole in the hub assembly. Movement of the selector arm about the connecting tip causes the hub assembly to rotate within the cam sleeve. When the cam pin reaches one end of the cam slot, further movement of the selector arm about the frangible connecting tip is prevented. Continued movement of the selector arm causes the selector arm to pivot about the drive pin thus causing the frangible connecting tip to become severed from the remainder of the hub assembly. Further movement of the selector arm causes the combination of the needle and the frangible connecting tip to become aligned with an ambient air passageway formed in the hub assembly. The ambient air passageway is sized to permit the needle and hub assembly to drop down through the passageway and into the air compensating region of the far region. Thus, in one motion the needle is severed from the hub assembly and dropped into the air compensating region to promote the safe disposal of the syringe.

The present invention has been discussed primarily in terms of a liquid being drawn into a partial vacuum region containing a powdered or granular solid. However, the invention also may be carried out by reversing the locations of the liquid and dry components. In such event a second floating gasket could be used between the liquid (which would be adjacent the barrier) and the plunger. A space between the plunger and the second floating gasket would act as an air spring to place the liquid under pressure. Pushing the plunger towards the second floating gasket would pressurize the liquid so that opening a pathway in the barrier would allow the pressurized liquid to rush into the far region containing the other component. The invention could be used with two liquids rather than a liquid and a solid. Veterinary as well as human uses are contemplated.

Other features and advantages of the invention will be apparent from the following description in which the preferred embodiment has been set forth in detail in conjunction with the accompanying drawings.

BRIEF DESCRIPTION OF THE DRAWINGS

FIG. 1 is an exploded isometric view of a hydrating syringe made according to the invention;

FIG. 2 an assembled isometric view of the syringe of FIG. 1;

FIG. 5 illustrates the syringe of FIG. 4 after a partial vacuum has been drawn within the near region of the bore;

FIGS. 6A and 6B are top plan and cross-sectional views of the syringe of FIG. 5 showing the movement of the selector arm from a dashed line sealing position to a solid line open position to permit the liquid within the liquid region of the bore to move into the near region of the bore creating violent, turbulent mixing of the liquid and dry components within the near region;

FIG. 7 shows the syringe of FIG. 6A while moving the mixture between the near and far regions of the bore;

FIGS. 8A and 8B are top plan and cross-sectional views of the syringe of FIG. 7 shown with the mixture drawn into the near region of the bore and the selector arm moved back to the sealing position of FIG. 5 and the sheath removed from the needle in preparation for injecting the medicine mixture into a patient;

FIG. 9A is a top view of the syringe of FIG. 8A illustrating the movement of the selector arm from the dashed line sealing position, to the dashed line open position and finally to the solid line disposal position; and FIG. 9B is taken along line 9B—9B of FIG. 9A and illustrates the severance of the frangible connecting tip from the remainder of the hub assembly and the dropping of the used needle through the ambient air passageway formed in the hub assembly and into the air compensating region of the far region of the bore.

DETAILED DESCRIPTION OF THE PREFERRED EMBODIMENT

Figure 3A:
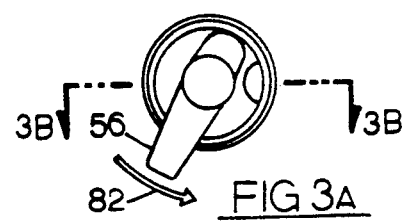
FIG. 3A is a top plan view of the syringe of FIG. 2 with the selector arm in the sealing position.

Referring the reader's attention to FIGS. 1, 2, 3A and 3B, a hydrating syringe 2 is shown to include a clear barrel 4 having a needle end 6, a plunger end 8 and defining a bore 10. Barrel 4 is preferably clear, to permit the contents to be seen, and of a medically approved material, such as polypropylene, polycarbonate or glass. A finger cap 12 is mounted to the plunger end 8. A barrier 14 is mounted along bore 10 to divide bore 10 into a far region 16 between barrier 14 and needle end 6 and a near region 18 between barrier 14 and plunger end 8. A plunger 20 is mounted within near region 18 and includes a plunger body 22 and a plunger gasket 24. The forward face 26 of plunger gasket 24 has a number of arcuate turbo blades 28 extending therefrom. The turbo blades are expected to help create additional turbulence during mixing, as is discussed below.

A cam sleeve 30 is secured to needle end 6. Sleeve 30 includes a generally spirally oriented cams slot 32 having a pair of detents 34 at either end. Cam slot 32 extends around about one-quarter of the circumference of cam sleeve 30. A hub assembly 36 is rotatably mounted within cam sleeve 30. Hub assembly 36 includes a lower hub 38 and an upper hub 40 capturing a filter 42 therebetween. As illustrated best in FIG. 3B, lower hub 38 has a cavity 44 within which filter 42 and a lower extension 46 of upper hub 40 extend. Lower and upper hubs 38, 40 are secured to one another, typically with an adhesive. Hub assembly 36 is captured within cam sleeve 30 through the passage of a cam pin 48 into cam slot 32. Thus, rotation of hub assembly 36 within cam sleeve 30 causes hub assembly 36 to move axially within cam sleeve 30.

Hub assembly 36 also includes a frangible connecting tip 50 to which the base 52 of a needle 54 is mounted. Hub assembly 36 is rotated within cam sleeve 30 by a selector arm 56 mounted to upper hub 40. Selector arm 56 includes a transverse portion 58 having a hollow guide 60. Portion 58 has a hole through which tip 50 passes while needle 54 passes through guide 60. Selector arm 56 also includes a drive pin 62 which engages an eccentric hole 64 formed in hub assembly 36. To rotate hub assembly 36 and needle 54 therewith, the user grasps an axially extending portion 66 of selector arm 56 and rotates selector arm 56 causing cam pin 48 to move along cam slot 32 thus driving hub assembly 36, and needle 54 secured thereto, axially. A sheath 68 is mounted over needle 54 for protection.

Figure 3B:
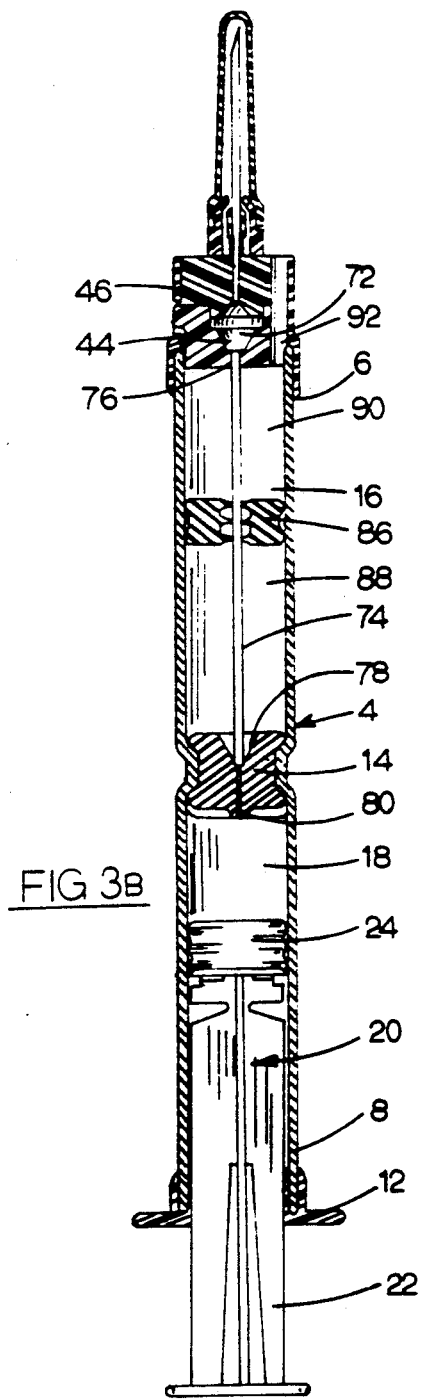
FIG. 3B is the cross-sectional view of the syringe of FIG. 2 taken along line 3B—3B of FIG. 3A with the plunger partially withdrawn.

As shown in FIG. 3B, hub assembly 36 defines a through passage 72 therethrough. A hollow tube 74, typically glass, is mounted to and carried by one end 76 of hub 38. Tube 74 extends along far region 16 to engage a valve seat 78 at the end of a pathway 80 formed in barrier 14 when selector arm 56 is in the sealing position of FIGS. 2, 3A and 3B. Movement of selector arm 56 in the direction of arrow 82 moves hub assembly 36 and tube 74 therewith axially away from barrier 14, thus opening pathway 80.

Tube 74 is guided along its length by a freely floating gasket 86 which divides far region 16 into a liquid region 88 and an air compensating region 90. Region 90 is connected to the ambient environment by an ambient air passageway 92 formed in hub assembly 36. Passageway 92 ensures that region 90 is maintained at atmospheric pressure.

Figure 4:
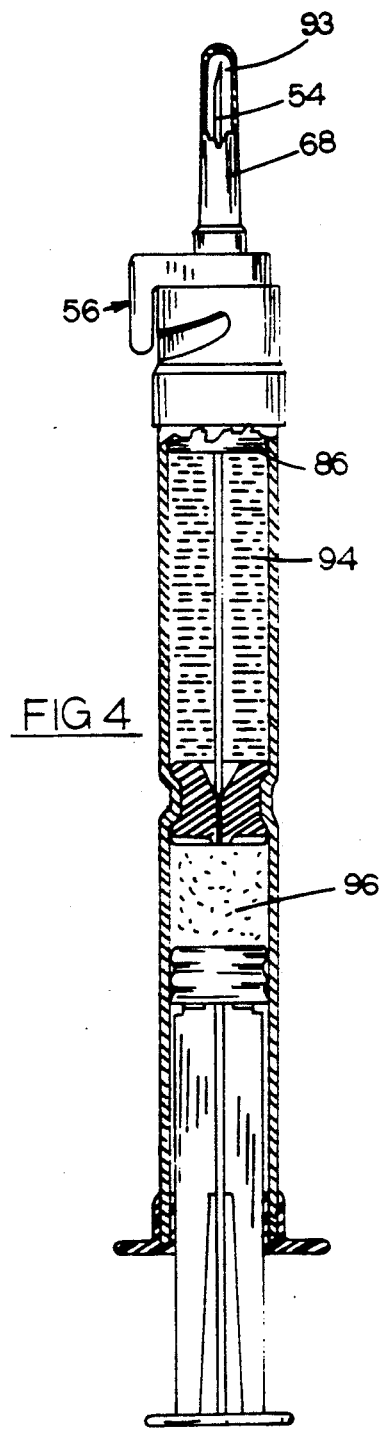
FIG. 4 shows a syringe of FIG. 3B with liquid and solid components stored within the syringe and the tip of the needle sealed.

Turning now to FIG. 4, a syringe 2 is shown in an as-packaged configuration. Sheath 68 includes a silicone sealant 93 at its tip so to seal needle 54 when mounted thereto. Also, a liquid component 94 is housed within liquid region 88 and a granular solid component 96 is housed within near region 18. To combine components 94, 96, the user first withdraws plunger 20 to the position of FIG. 5 as indicated by arrow 98 to create a partial vacuum within region 18. Plunger body 22 may be maintained in this position through the engagement appropriate catch structures formed at plunger end 8 of barrel 4 and plunger body 22 adjacent plunger gasket 24. The user then rotates selector arm 56 in the direction of arrow 82 to the open position of FIGS. 6A and 6B thus placing syringe in its mixing configuration. Doing so moves hub assembly 36 and tube 74 axially away from barrier 14 to permit liquid component 94 to very quickly rush through pathway 80 and into near region 18 in an energetic, turbulent manner as suggested in FIG. 6B. Note that the rush of liquid 94 from liquid region 88 into near region 18 is relatively unrestricted by floating gasket 86 because floating gasket 86 readily moves along the length of far region 16 and the air compensating region 90 is maintained at atmospheric pressure. This movement of floating gasket 86 is suggested by arrows 104.

The partial vacuum within region 18 creates very effective turbulent mixing between components 94, 96. However, by leaving selector arm 56 in the open position of FIG. 6A, the user can manipulate plunger 20 as suggested in FIG. 7 to cause the resulting mixture 106 to flow back and forth through pathway 80 between near region 18 and liquid region 88. The movement of the mixture is preferably in an turbulent, mixing manner.

Mixing is intended to be enhanced by the provision of turbo blades 28 on forward face 26 of plunger gasket 24. Similarly, barrier 14 includes a turbulence enhancer 108 on its surface facing near region 18 which is designed to increase the turbulence of mixture 106 within syringe 2.

To prepare for injecting mixture 106, the user withdraws plunger 20 until all of mixture 106 is within near region 18. See FIG. 8B. Selector arm 56 is then rotated in the direction of arrow 110 which forces tube 74 in the direction of arrow 112 and into engagement with valve seat 78. Sheath 68 is then removed as suggested in FIG. 8B. Syringe 2 is now ready to inject medicine mixture 106 by forcing plunger 20 into near region 18 which forces mixture 106 through pathway 80, tube 74, passage 72 and finally through needle 54.

Once syringe 2 has been used, the syringe can be destroyed in a manner to prevent its further use and to help prevent injury from needle 54. This is accomplished as shown in FIGS. 9A and 9B by placing syringe 2 in an upright, vertical orientation as illustrated in the figures, moving selector arm 56 in the direction of arrow 82 from the dashed line sealing position 114 to the dashed line open position 116; engagement of cam pin 48 with the end of cam slot 32 prevents the further movement of arm 56 about the main axis 120 of syringe 2. However, by forcing selector arm 56 in the direction of arrow 118, selector arm 56 pivots about the offset axis 122 of drive pin 62 causing frangible connecting tip 50 to break away from upper hub 40. Selector arm 56 continues moving until arm 56 attains the solid line disposal position 124 of FIG. 9A. At this point, needle 54 and frangible connecting tip 50 therewith overlie ambient air passageway 92 in hub assembly 36. Retainer 60 relatively loosely encircles tip 50 and the base of needle 54 so that the needle drops down by gravity into the air compensating region 90 as indicated in FIG. 9B for safe disposal.

Modification and variation may be made to the preferred embodiment without departing from the subject of the invention as defined in the following claims. For example, instead of using floating gasket 86, liquid component 94 could be held within a freely collapsible bag or bladder within far region 16. In the preferred embodiment the same component, tube 74, is used to provide the fluid pathway for the passage of mixture 106 into needle 54 and to seal pathway 80 formed in barrier 14. If desired, a tube connecting through passage 72 with near region 18 could be used to provide continuous, or selective, fluid connection and a separate valve could be used to couple liquid region 88 and near region 18.

What is claimed is:

1. A component mixing syringe, for use in mixing a first, liquid component with a second component, comprising:
    a barrel having a bore, a plunger end and a needle end;
    a stationary barrier dividing the bore into a near region between the barrier and the plunger end and a far region between the barier and the needle end, the first component being stored in one of the near and far regions and the second component being stored in the other of the near and far regions;
    a plunger mounted in the bore at the plunger end for creating a partial vacuum within the near regions;
    means for selectively fluidly coupling the near and far regions so any differential pressure between the near and far regions causes turbulent mixing between the first and second components;
    a hollow needle mounted to the needle end;
    means for selectively sealing the needle form the atmosphere; and
    a flow path element defining a flow path fluidly coupling the needle directly to the near region so that the mixed first and second components can be injected through the needle by manipulation of the plunger.

2. The syringe of claim 1 wherein the first, liquid component is stored in the far region.

3. An improved component mixing syringe structure, by which a first, liquid component can be mixed with a second component prior to use, comprising:
    a barrel having a hollow interior, a plunger end and a needle end;
    a needle mountable to the needle end of the barrel, the needle having a hollow interior, a liquid delivery end and a liquid receiving end;
    means for selectively sealing the needle end from the atmosphere;
    a plunger slidably mounted within the interior at the plunger end;
    a valve barrier assembly, manipulable between mixing and sealed configurations, including a barrier positioned along the interior to divide said interior into a far region towards the needle end and a near region, the valve barrier assembly including a pathway fluidly coupling the far and near regions when the valve barrier assembly is in the mixing configuration and fluidly separating the far and near regions when in the sealed configuration;
    a flow path element defining a flow path fluidly connecting the near region with the liquid receiving end; and
    means for dividing the far region into a variable volume air compensating region and a variable volume liquid region, the air compensating region fluidly coupled to the ambient environment to keep the air compensating region at the ambient environment pressure;
    whereby partially withdrawing the plunger from the near region of the interior of the barrel while the valve barrier assembly is in the sealed configuration and the selectively sealing means seals the needle end from the atmosphere creates a partial vacuum within the near region so that placing the valve barrier assembly in the mixing configuration permits the first, liquid component int eh liquid region to quickly flow into the near region to mix with the second component in the near region, the first and second components being further mixable by moving the plunger within the near region, and the components being deliverable through the connecting means and through the hollow interior of the needle.

4. The syringe structure of claim 3 wherein the dividing means includes a floating gasket positioned at and freely movable along the far region.

5. The syringe structure of claim 3 wherein the sealing means is a sheath for sealably covering the liquid delivery end of the needle to permit said partial vacuum to be created in the near region.

6. The syringe structure of claim 5 wherein the barrier defines a valve seat along the pathway; and
wherein the valve barrier assembly further includes:
an axially movable, hollow needle mount, mounted to the needle end of the barrel, to which the needle is secured, the needle mount being movable relative to the barrel between first and second axial positions; and
a connecting tube, mounted to the needle mount and movable therewith, having an end which seats with the valve seat when the needle mount is in the first axial position thereby sealing the near region from the far region and also fluidly coupling the near region with the needle through the connecting tube and the hollow needle mount, said end of the connecting tube being displaced from the valve seat when the needle mount is in the second axial position thereby fluidly coupling the near and far regions through the pathway.

7. The syringe structure of claim 6 wherein the needle mount includes:
a cam sleeve, mounted to the needle end of the barrel, having a generally spiral shaped cam slot formed therein; and
a hollow hub assembly mounted within the cam sleeve and defining an axial bore, the connecting tube mounted to one end of the hub assembly, the needle mounted to the other end of the hub assembly and fluidly coupled to the connecting tube by the axial bore, the hub assembly including a cam pin housed within the cam slot;
whereby rotating the hub assembly within the cam sleeve causes the needle mount to move between the first and second axial position.

8. The syringe of claim 3 wherein the barrier includes a turbulence enhancer facing the near region.

9. An improved component mixing syringe, by which a first, liquid component can be mixed with a second component prior to use, comprising:
a barrel having a needle end, a plunger end and a bore;
a plunger mounted within the bore;
a barrier dividing the bore into a near region between the barrier and the plunger and a far region between the barrier and the needle end;
a hollow needle mounted to the barrel at the needle end;
means for selectively sealing the hollow needle from and connecting the hollow needle to the atmosphere;
a flow path element defining a flow path fluidly coupling the needle with the near region;
means for dividing the far region into a variable volume air compensating region and a variable volume liquid region;
an ambient air passageway coupling the air compensating region to an ambient environment;
valve means for selectively fluidly coupling and separating the near region and the liquid region when in coupled and separated states respectively;
control means for selectively preventing fluid passage along the flow path when in a closed state and for permitting fluid passage along the flow path when in an open state;
whereby when the valve means is in the separated state and the control means is in the closed state and the plunger is partially withdrawn form the bore, a partial vacuum is created within the near region so that placing the valve means in the coupled state causes at least a part of the first, liquid component within the liquid region to quickly flow into the near region to mix in a turbulent manner with the second component, the mixing being further enhanced by pushing the plunger into and withdrawing the plunger from the bore thereby forcing the mixture through the selectively fluidly coupling means; and
the mixture being injectable through the needle when the mixture is in the near region, the control means is in the open state, the selectively sealing means is connecting the hollow needle to the atmosphere, and the valve means is in the separated state.

10. The syringe of claim 9 further comprising means for shearing the needle from the flow path element.

11. The syringe of claim 10 further comprising means for dropping the sheared needle into the air compensation region.

12. The syringe of claim 9 wherein the needle includes a tip and the control means includes a sheath mountable over the needle and to seal the tip of the needle.

13. A method for mixing a first, liquid component with a second component within a syringe to create a mixture, the mixture to be dispensed by the syringe through a hollow needle, comprising:
providing a syringe with a first region, for containing the first component, and a second region, for containing the second component, the first and second regions separated by a barrier element;
sealing the hollow needle form the atmosphere;
creating a partial vacuum within the second region;
fluidly coupling the first and second regions through a path in the barrier element to permit the turbulent mixing of the first and second components to create the mixture;
fluidly coupling the second region to the hollow needle through a flow path element passing through the first region; and
dispensing the mixture from the second region, through the flow path element and through the hollow needle.

14. The method of claim 13 wherein the second component is a dry component.

15. The method of claim 13 further comprising the step of forcing the mixture between the first and second regions to ensure thorough mixing.

16. The method of claim 13 further comprising the step of separating the needle from the remainder of the syringe after use and depositing the separated syringe into first region to aid safe disposal of the used syringe.

17. An improved component mixing syringe structure, by which a first, liquid component can be mixed with a second component prior to use, comprising:

a barrel having a hollow interior, a plunger end and a needle end;

a plunger slidably mounted within the interior at the plunger end;

a valve barrier assembly, manipulable between mixing and sealed configurations, including a barrier positioned along the interior to divide said interior into a far region towards the needle end and a near region, the valve barrier assembly including a pathway fluidly coupling the far and near regions when the valve barrier assembly is in the mixing configuration and fluidly separating the far and near regions when in the sealed configuration;

means for dividing the far region into a variable volume air compensating region and a variable volume liquid region, the air compensating region fluidly coupled to the ambient environment to keep the air compensating region at the ambient environment pressure;

a needle having a hollow interior, a liquid delivery end and a liquid receiving end;

means for selectively sealing the hollow interior of the needle from the atmosphere;

a flow path element for fluidly connecting the near region with the liquid receiving end;

an axially movable, hollow needle mount, mounted to the needle end of the barrel, to which the needle is secured, the needle mount being movable relative to the barrel between first and second axial positions; and wherein the needle mount further includes;

a cam sleeve, mounted to the needle end of the barrel, having a generally spiral shaped cam slot formed therein; and a hollow hub assembly mounted within the cam sleeve and defining an axial bore, the connecting means mounted to one end of the hub assembly, the needle mounted to the other end of the hub assembly, and fluidly coupled to the connecting means by the the axial bore, the hub assembly including a cam pin housed within the cam slot;

whereby rotating the hub assembly within the cam sleeve causes the needle mount to move between the first and second axial position.

18. The syringe of claim 17 wherein the cam slot is a through slot.

19. The syringe of claim 17 wherein the hub assembly includes a filter positioned along the axial bore.

20. The syringe structure of claim 17 wherein the needle mount further includes a selector arm mounted to the hub assembly for rotating the hub assembly within the cam sleeve.

21. The syringe structure of claim 20 wherein the selector arm includes a hole, the hub assembly includes a connecting tip housed within the hole, and the selector arm includes an eccentric drive pin which engages the hub assembly so that rotating the selector arm between the first and second rotary positions, corresponding to the first and second axial positions of the needle mount, causes the hub assembly to rotate therewith.

22. The syringe structure of claim 21 wherein the connecting tip is a frangible connecting tip so that forcing the selector arm past at least one of the first and second rotary positions causes the frangible connecting tip to break away from the rest of the hub assembly thereby destroying the utility of the syringe structure.

23. The syringe structure of claim 22 wherein the hub assembly includes an axial ambient air passageway coupling the ambient environment with the air compensating region, the passageway sized for insertion of the needle therethrough after the frangible connecting tip has been broken, thus freeing the needle from the hub assembly.

* * * * *